United States Patent
Anderhub et al.

[11] Patent Number: 5,906,630
[45] Date of Patent: May 25, 1999

[54] ECCENTRIC SURGICAL FORCEPS

[75] Inventors: Otto E. Anderhub; Boris Kesler; Rey Sylvester, all of Miami, Fla.

[73] Assignee: Boston Scientific Limited, St. Michael, Barbados

[21] Appl. No.: 09/107,135

[22] Filed: Jun. 30, 1998

[51] Int. Cl.⁶ .................................................. A61B 17/28
[52] U.S. Cl. .................. 606/205; 606/207; 606/153; 606/208
[58] Field of Search ................... 606/205, 207, 606/153, 208

[56] References Cited

U.S. PATENT DOCUMENTS

| | | | |
|---|---|---|---|
| 5,192,298 | 3/1993 | Smith et al. | 606/205 |
| 5,201,759 | 4/1993 | Ferzli | 606/207 |
| 5,219,357 | 6/1993 | Honkanen et al. | 606/205 |
| 5,241,968 | 9/1993 | Slater | 128/751 |
| 5,263,967 | 11/1993 | Lyons, III et al. | 606/205 |
| 5,282,826 | 2/1994 | Quadri | 606/207 |
| 5,312,432 | 5/1994 | Pingleton et al. | 606/205 |
| 5,338,317 | 8/1994 | Hasson et al. | 606/206 |
| 5,342,389 | 8/1994 | Haber et al. | 606/205 |
| 5,395,364 | 3/1995 | Anderhub et al. | 606/51 |
| 5,423,854 | 6/1995 | Martin et al. | 606/205 |
| 5,507,773 | 4/1996 | Huiteman et al. | 606/207 |
| 5,571,137 | 11/1996 | Marlow et al. | 206/207 |
| 5,582,617 | 12/1996 | Klieman et al. | 606/170 |
| 5,591,182 | 1/1997 | Johnson | 606/151 |
| 5,601,578 | 2/1997 | Murphy | 606/148 |

*Primary Examiner*—Michael Buiz
*Assistant Examiner*—Tan-Uyen T. Ho
*Attorney, Agent, or Firm*—Finnegan, Henderson, Farabow, Garrett, and Dunner, L.L.P.

[57] ABSTRACT

A surgical forceps which can be used for taking biopsy specimens internally is described having a compact configuration and very wide opening jaws, both of which are movable together by means of an elongated, flexible actuator member which operates directly only on one of the two end effectors containing the respective jaws. The forceps is particularly useful in conjunction with a surgical scope such as an endoscope or similar device.

24 Claims, 9 Drawing Sheets

ECCENTRIC SURGICAL FORCEPS

FIELD OF THE INVENTION

The present invention relates to surgical instruments, such as forceps having a distal assembly for performing internal surgical procedures involving cutting, grasping, and/or removing internal tissue. More particularly, the present invention relates to biopsy forceps, having articulated end effectors, for cutting and/or removing tissue samples.

BACKGROUND OF THE INVENTION

Surgical procedures involving the cutting, grasping, and/or removal of internal tissue are frequently performed using various forms of surgical forceps which may be passed into the body through an elongated, usually flexible tube, such as an endoscope, catheter, cannula, or trocar. Examples of endoscopes used in these procedures are laparoscopes, thorascopes, and arthroscopes. Typical of such forceps is a bioptome used to remove biopsy specimens internally. The bioptome includes a long flexible coil having a pair of opposed jaws at the distal end and a manual actuator at the proximal end. Manipulation of the actuator opens and closes the jaws. During biopsy tissue sample procedures, the bioptome, or other surgical instrument, is inserted into the narrow lumen of an endoscope while viewing the biopsy site through an optical scope. The surgeon guides the endoscope to the biopsy site until the opposed jaws arrive at the biopsy site. The surgeon then positions the jaws of the bioptome around the tissue to be sampled and manipulates the actuator so that the jaws close around the tissue. A sample of the tissue is then cut or torn away from the biopsy site while it is trapped between the jaws of the bioptome. Keeping the jaws closed, the surgeon then withdraws the bioptome from the endoscope and opens the jaws to disgorge the biopsy tissue sample.

Because the lumen of the endoscope is usually relatively small, the bioptome inserted through the lumen must also be small and of compact configuration. Further, in order to achieve the necessary manipulation required to remove the sample and extract it through the lumen of the endoscope, the bioptome frequently has a fairly complex structure. Because of the size constraint and other limitations associated with the bioptome, the jaws typically open to a relatively narrow extent, thereby severely limiting the size and type of specimen that can be extracted. Some conventional bioptomes, for example, frequently employ a fixed jaw and a single movable jaw which closes against the fixed jaw. Other conventional bioptomes employ two movable jaws which are separately activated by complex, multi-link systems and which can only be opened to a relatively narrow extent.

The same considerations and constraints generally apply for other surgical forceps used for cutting, grasping, and/or removing internal tissue.

SUMMARY OF THE INVENTION

It is therefore an object of the invention to provide a surgical instrument for internally cutting, grasping, and/or removing tissue, the instrument having end effectors with jaws that can open relatively widely once inserted into an internal body area.

It is a further object of the invention to provide a surgical instrument for internally cutting, grasping, and/or removing tissue having end effectors with jaws that can be closed into a compact configuration to facilitate passage through the lumen of a surgical scope.

Additional objects and advantages of the invention will be set forth in the description which follows and, in part, will be apparent from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a surgical instrument, such as a surgical forceps, having a distal assembly for cutting, grasping, and/or taking internal body tissue that includes a proximal actuator assembly and a distal end effector assembly having first and second end effectors in which the proximal end of the second end effector pivotally engages the first end effector intermediate its proximal and distal ends. The two end effectors thereby form a pair of movable jaws in which the second end effector pivotally engages with the distal end of a clevis at a point intermediate its length. The clevis has an axial passage therethrough to accommodate a slidable, elongated actuator whose distal end is pivotally attached to the proximal end of the first end effector which is also slidably disposed in the distal end of the clevis. The proximal end of the clevis is adapted for attachment to the actuator assembly, which includes a tubular sheath containing a slidable, elongated cable that engages the proximal end of the actuator to permit axial displacement of the actuator and the end of the end effector to which it is attached, to cause the two jaws of the device to open or close.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate embodiments of the invention and together with the description serve to explain the principles of the invention.

DESCRIPTION OF THE PREFERRED EMBODIMENTS

Reference will now be made in detail to the present preferred embodiments of the invention, examples of which are illustrated in the accompanying drawings. Whenever possible, the same reference numbers will be used throughout the drawings to refer to the same or like parts.

The present invention is directed to an improved distal assembly for a surgical instrument and more particularly to surgical forceps having a distal assembly, for example, for taking biopsy specimens, and including a pair of end effectors that are interconnected to form a pair of jaws that can be widely opened and retracted to form a compact, linear unit that is compatible with the lumen of a surgical scope while also permitting wide opening of the jaws to facilitate their use once in place internally in a body.

The device of the invention can be employed in connection with various surgical scopes, trocars, cannulas, or catheters for removing, grasping, or cutting tissue specimens internally. Further, the distal assembly described herein is not limited in its application to surgical forceps, but can also be incorporated in other surgical devices having opposed jaws or cutting surfaces. Typical of devices useful in the invention are various graspers, surgical scissors, dissectors, clamps, and forceps.

Figure 1:
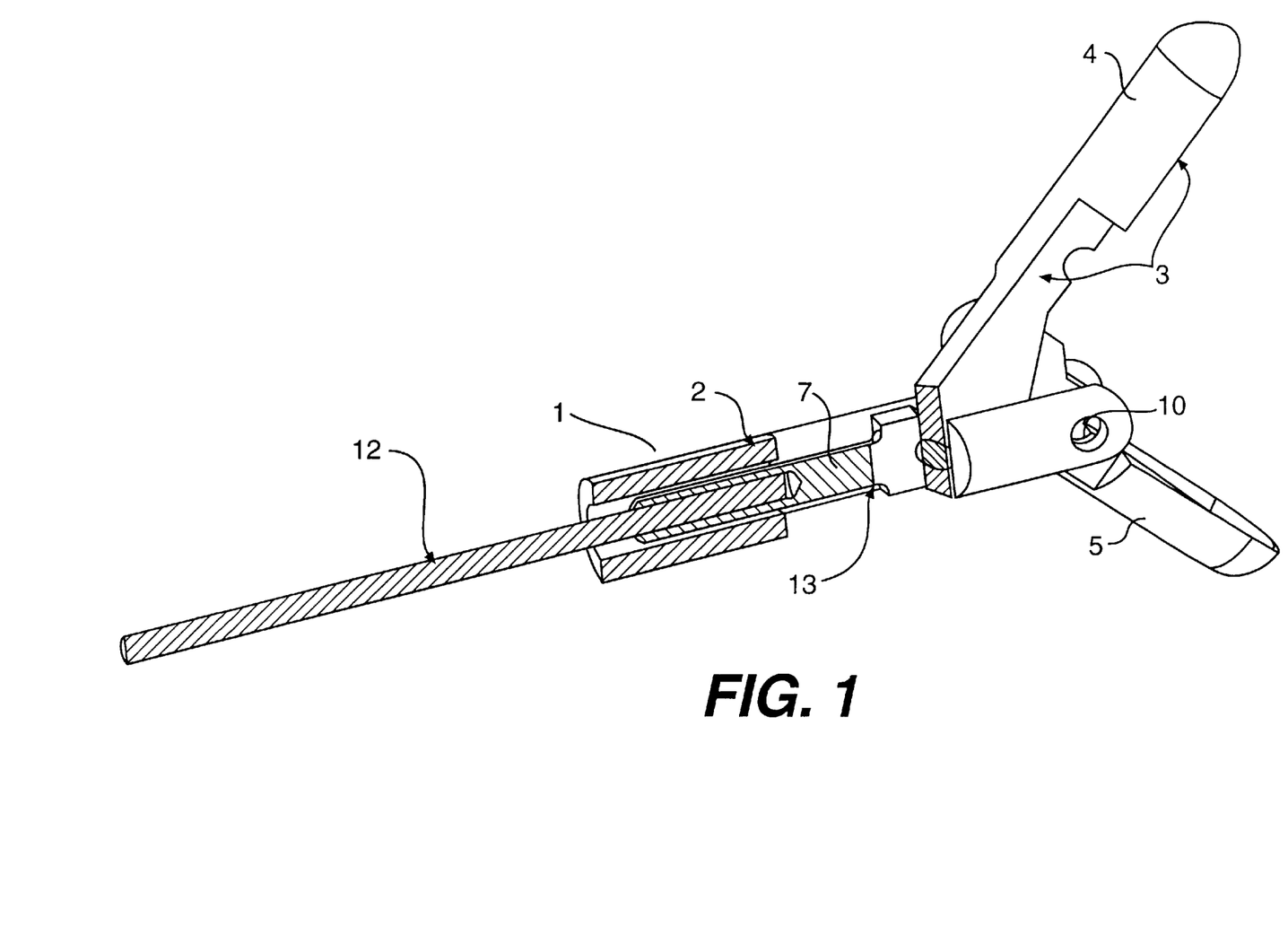
FIG. 1 is a partial cut-away perspective view showing one side of the distal assembly of the present invention with the respective jaws in an open configuration.

FIG. 1 of the drawings illustrates the distal assembly incorporated in surgical forceps in accordance with the present invention. The distal assembly 1 includes a clevis 2 having an actuator rod 7 slidably disposed within it and two end effectors 3 and 5 with opposing end portions 4 and 6 which, in the illustrated embodiment, are cup-shaped jaws having sufficiently sharp edges to facilitate the cutting, grasping, and removing of tissue samples when the respective end portions 4 and 6 are brought together by axial displacement of the actuator rod 7 whose distal end pivotally engages the proximal end of end effector 3 disposed within the clevis.

Figure 2:
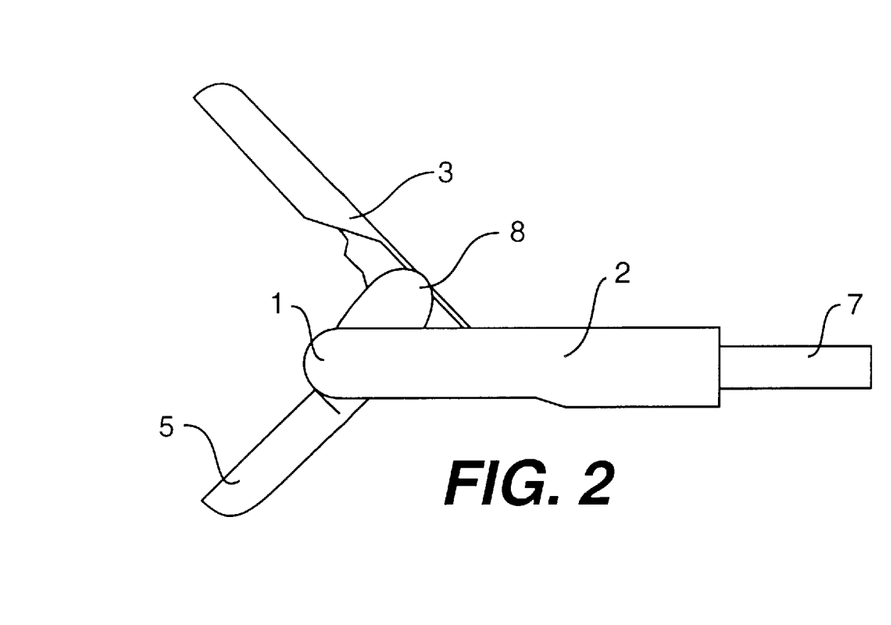
FIG. 2 is a side view illustrating an opposite side of the distal assembly shown in FIG. 1.
Figure 4:
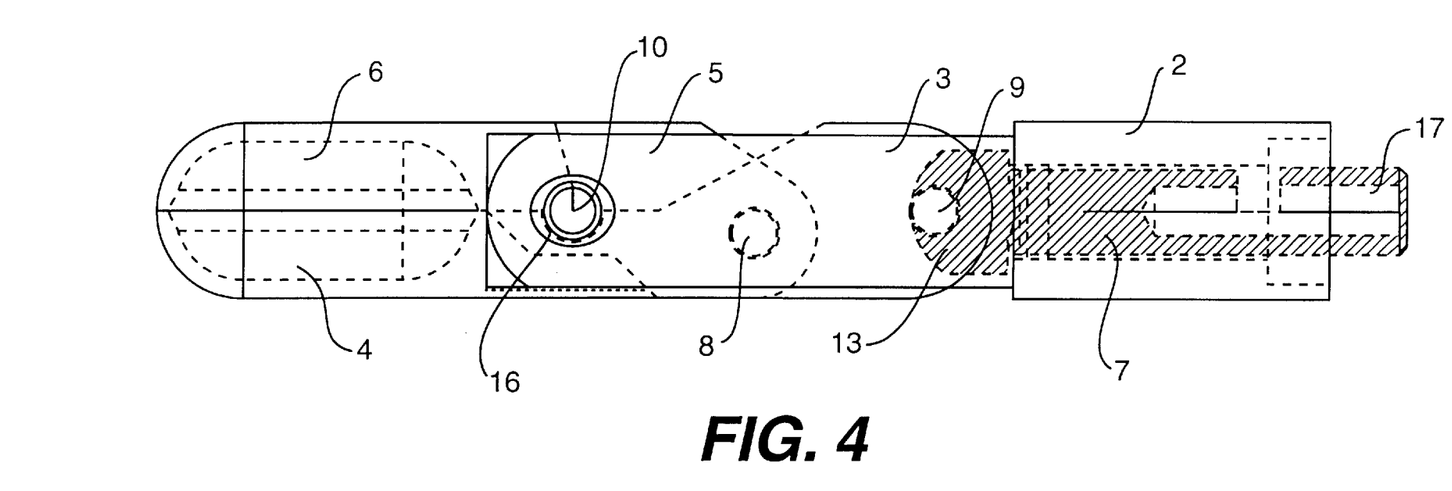
FIG. 4 is a side internal view of the internal component elements of the distal assembly of FIG. 1 with the assembly in the closed configuration.
Figure 5:
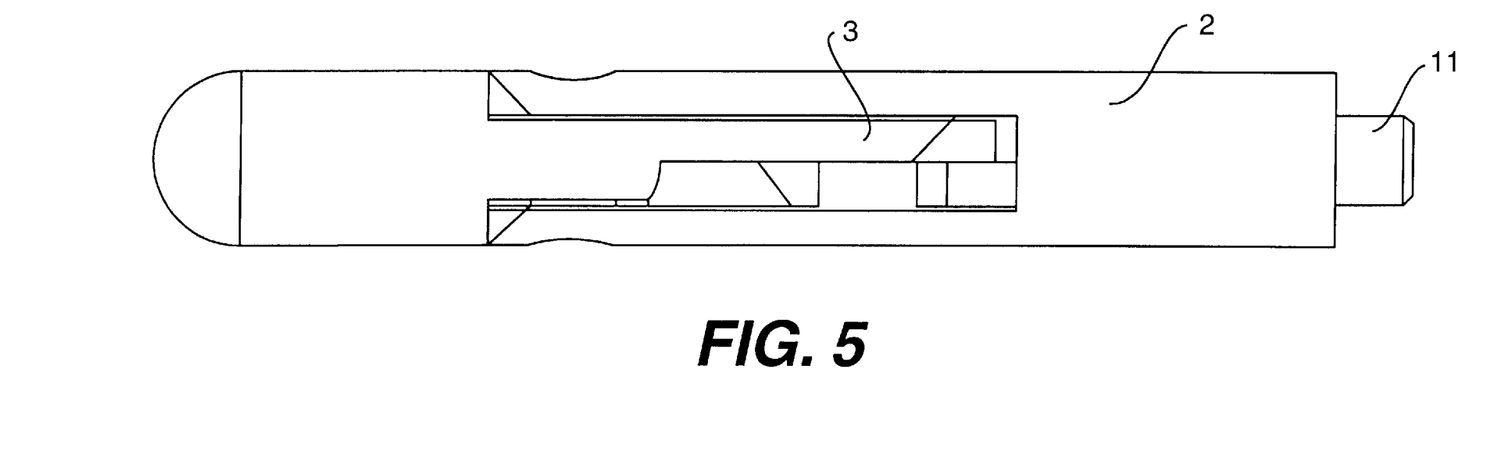
FIG. 5 is a bottom view of the assembly of FIG. 4.

FIG. 2 of the drawings illustrates the side of the surgical forceps of the invention opposite that shown in FIG. 1 and, in particular, illustrates the off-set, pivotal engagement of the proximal end of end effector 5 with end effector 3 at pivot point 8 intermediate the proximal and distal ends of end effector 3 resulting in pivot point 8 being out of axial alignment with actuator 7 in clevis 1 when the end effectors 3 and 5 are open as shown. When the end effectors 3 and 5 are closed together as shown in FIGS. 4 and 5, pivot point 8 is in axial alignment with the actuator 7 within the clevis 2.

Figure 3:
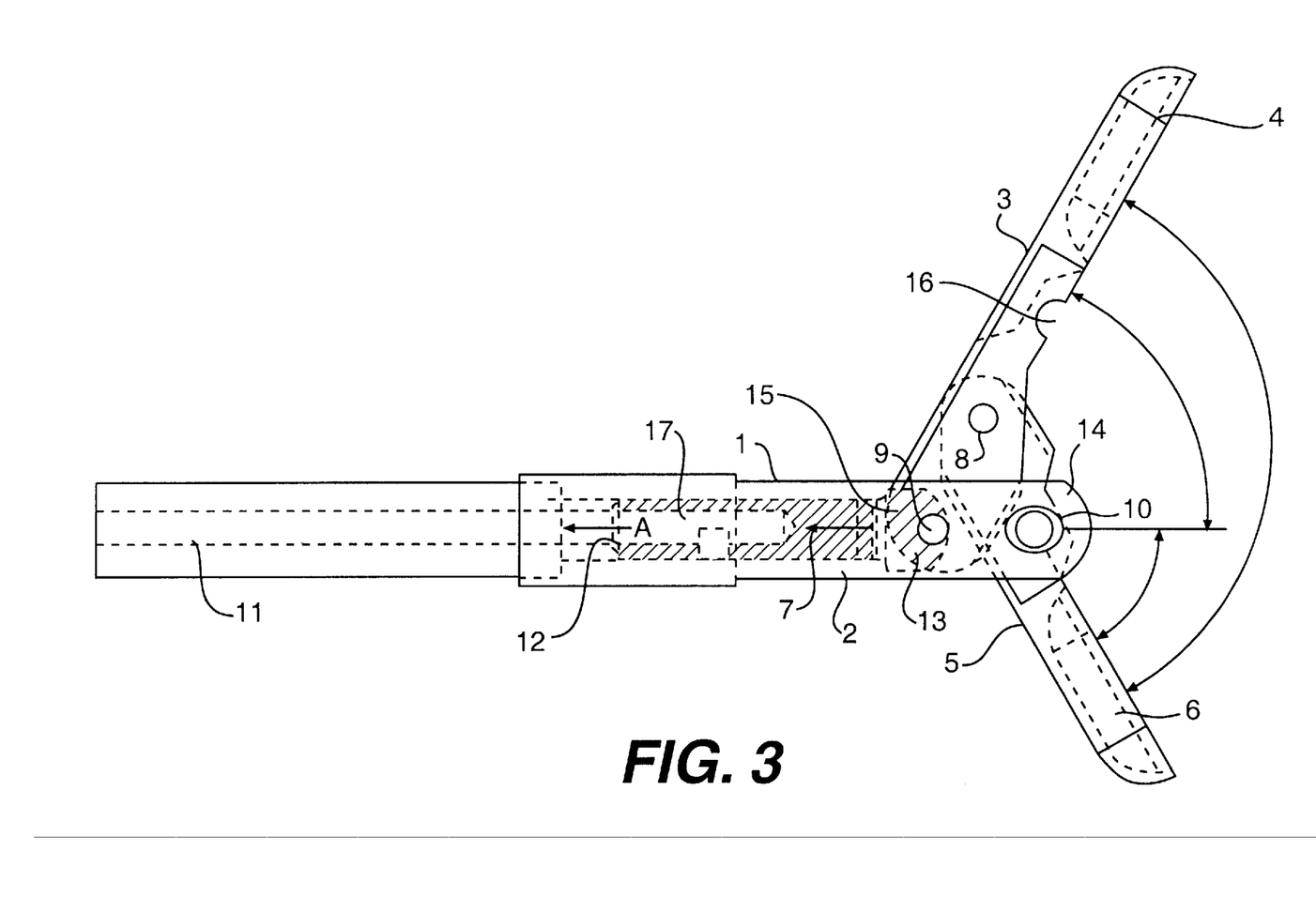
FIG. 3 is a side internal view of the component parts of the distal assembly of FIG. 1 with the jaws in the open configuration.
Figure 6:
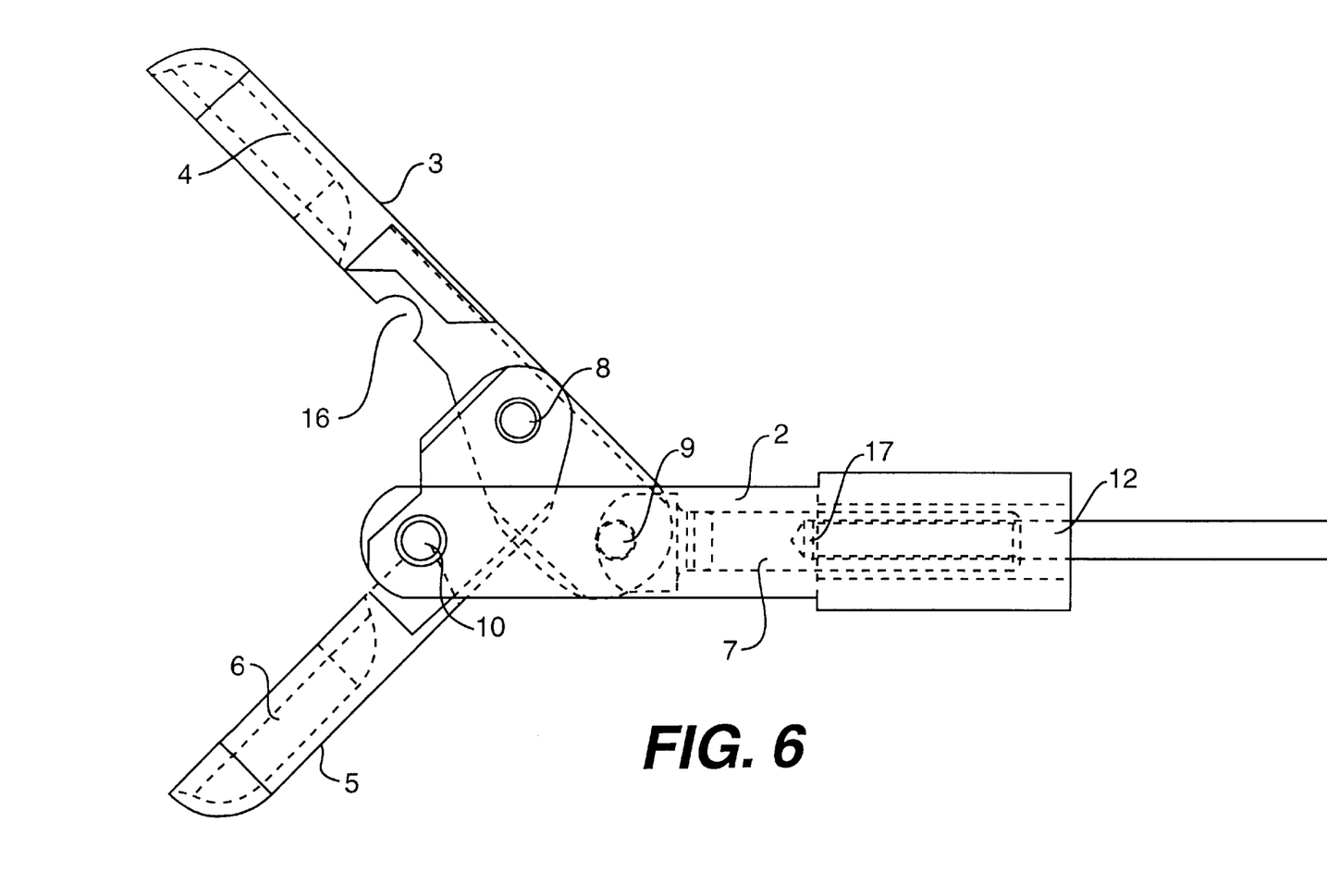
FIG. 6 is a side internal view illustrating the opposite side of the assembly of FIG. 1 with the jaws in the open configuration.
Figure 7:
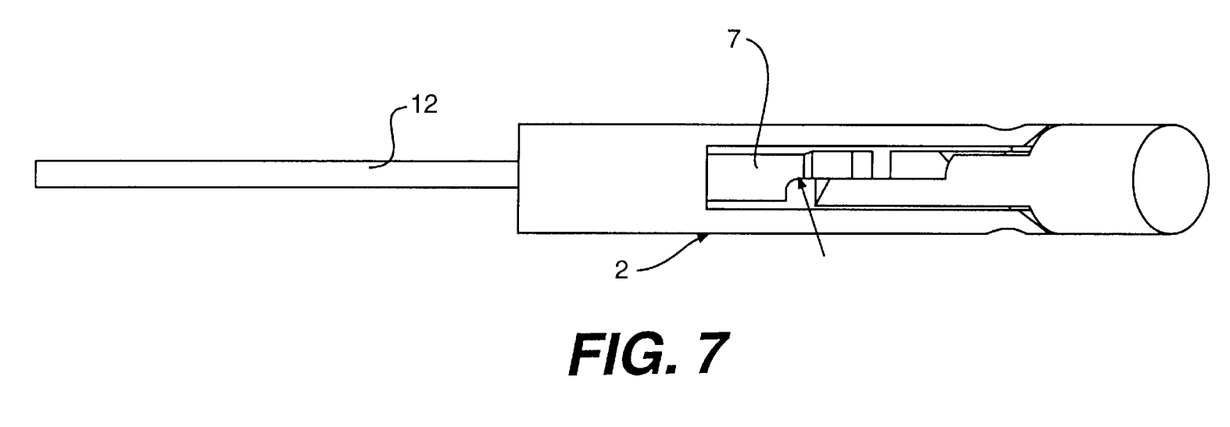
FIG. 7 is a top view of the distal assembly of FIG. 1.

The internal configuration of the distal assembly of the invention is shown in FIGS. 3 and 6, which are internal side views corresponding to FIG. 1. Distal assembly 1 includes an elongated clevis 2 having a distal end 14 and a pair of engaging end effectors 3 and 5. The shorter of the two end effectors 5 is pivotally attached at pivot point 10 to the distal end 14 of the clevis and also pivotally attached at pivot point 8 to the other end effector 3. As shown in FIG. 6, a cut-out slot 16 in effector 3 accommodates pivot point 10 when the end effectors are closed. End effector 3, which is the longer of the two end effectors, has a pivotal engagement at pivot point 9 with the distal end of actuator rod 7 which is slidably disposed within the clevis 2. Both of the end effectors 3 and 5 are provided with opposing end cups 4 and 6. The distal end of flexible, tubular sheath 11 is adapted to engage by any appropriate, known means, such as threading or fixed attachment, with the proximal end of clevis 2 and contains an elongated actuator cable 12 slidably disposed therein. Flexible cable 12 engages within channel 17 of actuator rod 7 to enable axial sliding movement of actuator rod 7 within the clevis 2 in response to axial movement of the actuator cable 12.

Movement of actuator rod 7 in the proximal direction (the direction of the arrow) causes movement in the proximal direction of the proximal end 15 of end effector 3. This axial movement by end effector 3, in the direction of the arrow, also causes pivotal rotation of end effector 3 around pivot point 8 and pivotal rotation of end effector 5 around pivot point 10 thereby causing the end effectors cups 4 and 6 to close towards one another until end effectors 3 and 5 are in opposing alignment in a compact linear configuration as illustrated in FIG. 4. Similarly, movement of the actuator rod 7 in the opposite or distal direction with respect to clevis 2 causes a sliding movement of proximal end 15 of end effector 3 which opens the jaws or end cups 4 and 6 of the device so that the opposing end effectors 3 and 5 are eventually widely separated. The various pivot points 8, 9, 10, and 22 are otherwise of conventional construction and can include, for example, any form of pin, bolt, or rotatable bearing.

Figure 9:
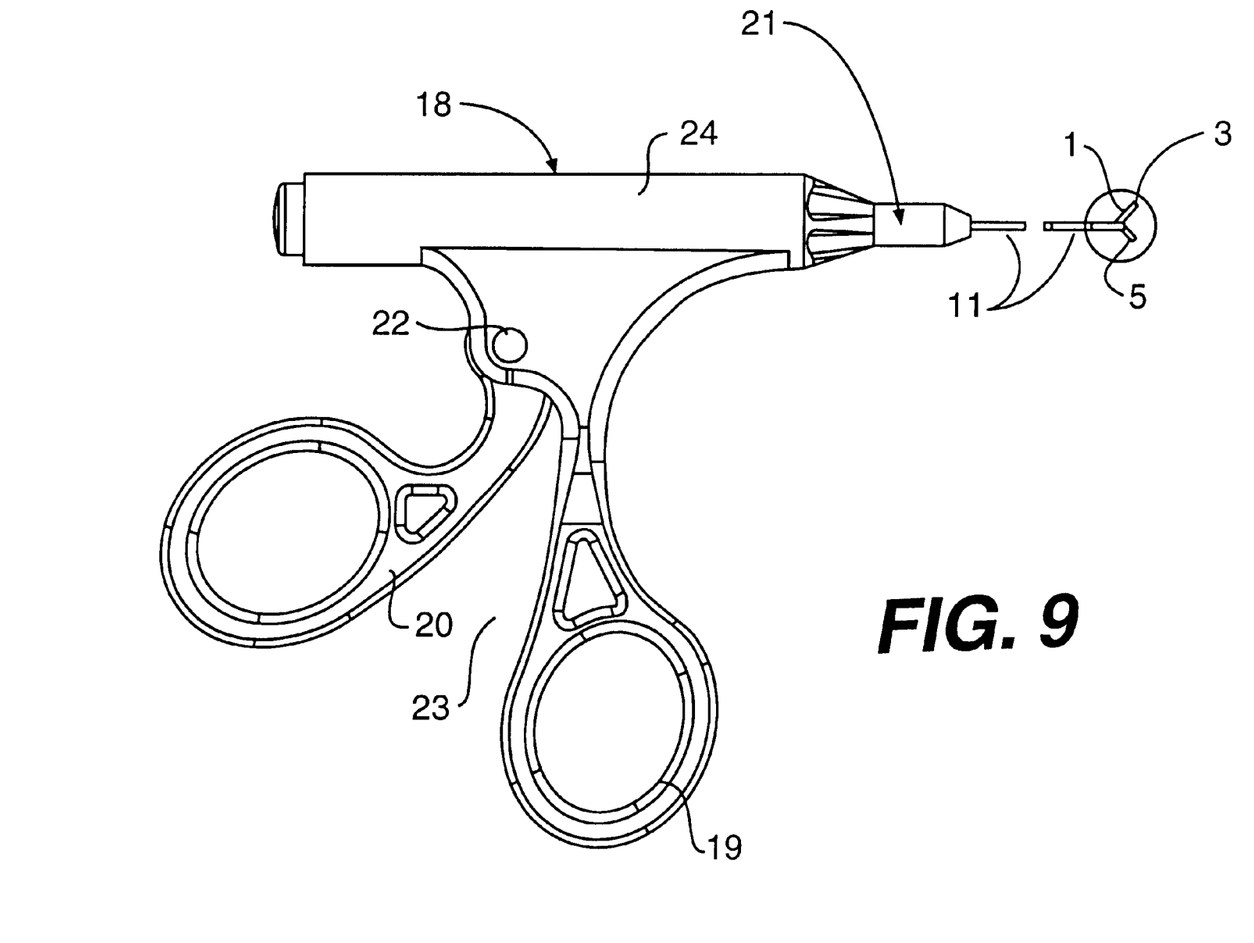
FIG. 9 is a side view of the entire surgical forceps of the invention with the distal end effector assembly in the open configuration.
Figure 10:
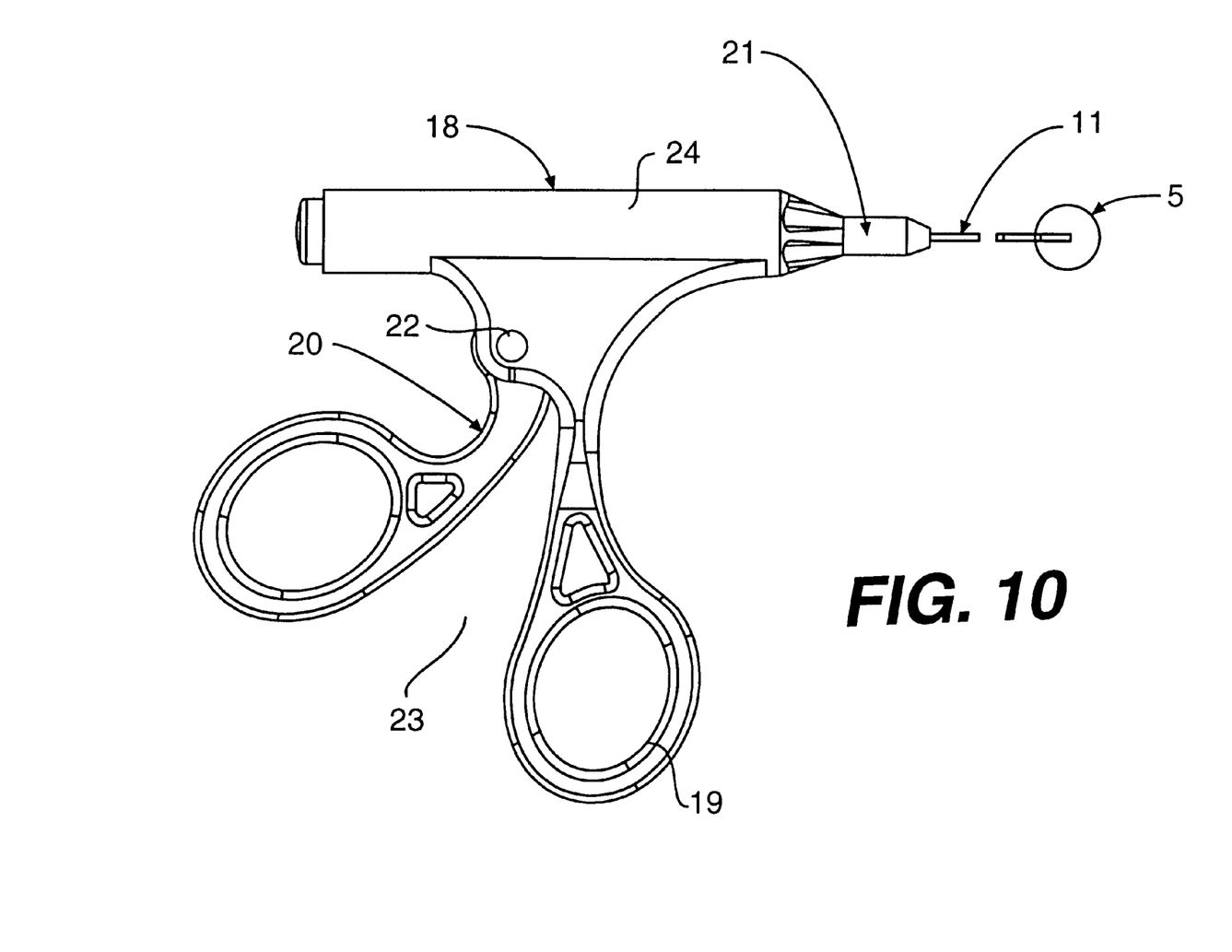
FIG. 10 is a side view of the entire surgical forceps of the invention with the distal end effector assembly in the closed configuration.

As shown in FIGS. 9 and 10, the proximal ends of sheath 11 and cable 12 terminate conveniently in a manipulator 18 having a handgrip 23 including fixed grip 19 attached to barrel 24 and moveable grip 20 which pivotally engages the barrel 24 at pivot point 22. The distal end (not shown) of grip 20 engages the proximal end of cable 12 (not shown) within barrel 24 such that movement of the proximal end of grip 20 toward or away from grip 19 results in axial movement of cable 12 within barrel 24 and tubular sheath 11 whose proximal end is attached by retainer 21 to barrel 24. Other forms of manipulators known in the art can also be employed to effect axial movement of cable 12 thereby opening or closing the jaws of the end effectors. For example, hand-grip 23 may be a conventional bioptome actuation device whose construction and operation are fully described in U.S. Pat. No. 5,542,432 to Slater et al., the complete disclosure of which is hereby incorporated by reference. Similarly, sheath 11 may be any conventional long, flexible coil-like section well known in the art for connecting a proximal handle to a distal end effector assembly. For example, the bioptome disclosed in the Slater et al. patent uses a long, flexible, and hollow coil with a control wire extending therethrough to couple the handle to an end effector assembly. The hollow coil may be manufactured from 304 steel wire by forming the wire over a mandrel. The use of the distal assembly described herein, however, is not limited to the actuation assembly disclosed in Slater et al. or any specific type of coil, and may be used in connection with various other actuation assemblies and coils known in the art.

As noted, FIG. 4 of the drawing is an internal view of the surgical forceps of the invention in collapsed configuration. The two opposing cups or jaws 6 and 4 are pressed against one another and the two end effectors 3 and 5 are in close alignment substantially within the confines of the clevis 2.

Figure 8:
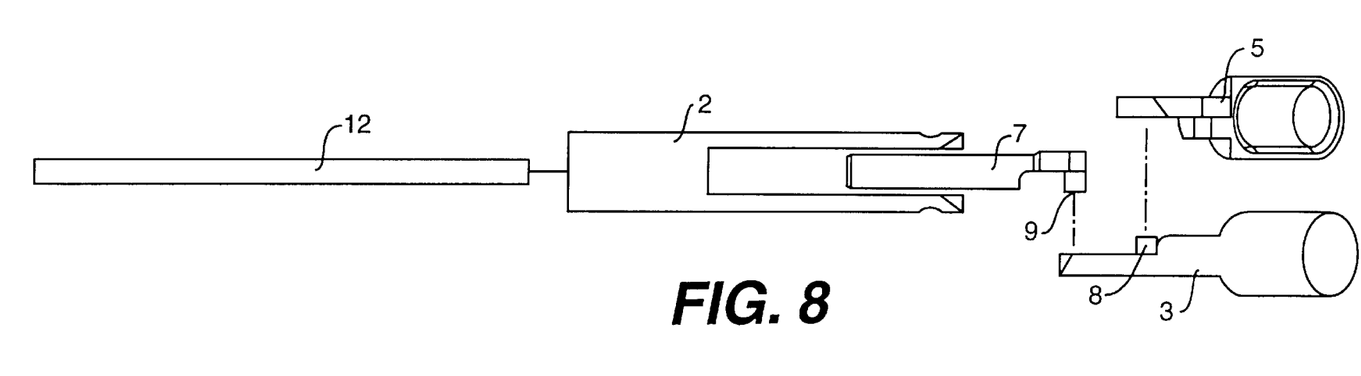
FIG. 8 is an exploded top view of the assembly of FIG. 1.

FIG. 5 of the drawings further illustrates from the bottom the closed configuration of the surgical forceps of the invention. (FIGS. 4 and 5 do not show the tubular sheath 11 shown in FIGS. 8 and 9.)

Figure 11:
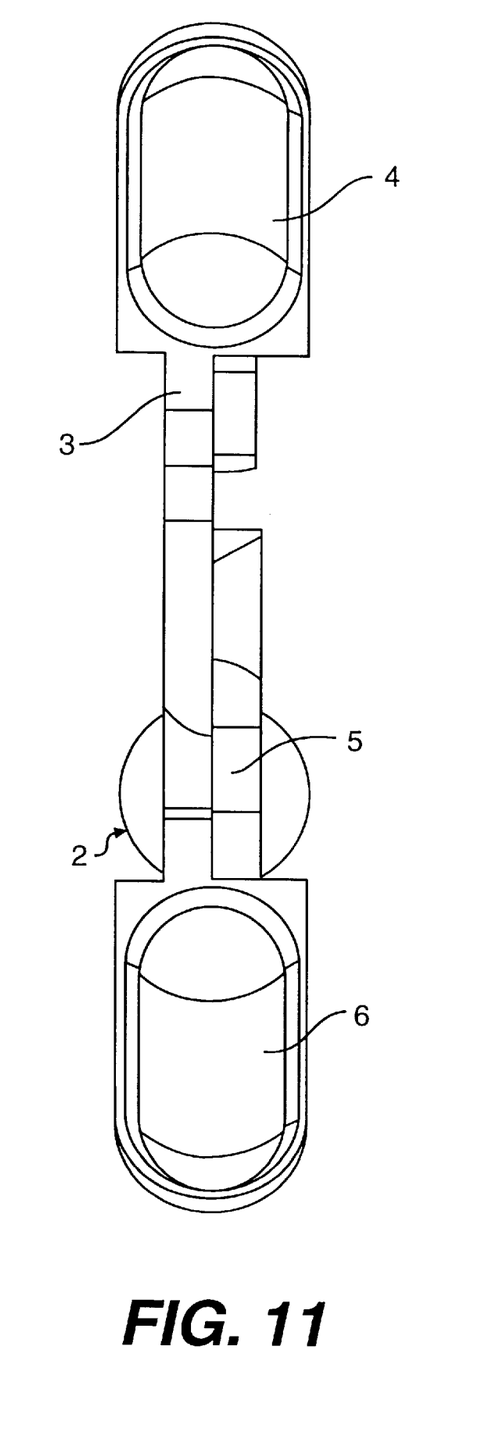
FIG. 11 is a front view of the assembly of FIG. 1 with the jaws in open configuration.

FIG. 11 of the drawings illustrates the surgical biopsy forceps of the invention in the open configuration as viewed from the front of the device.

Figure 12:
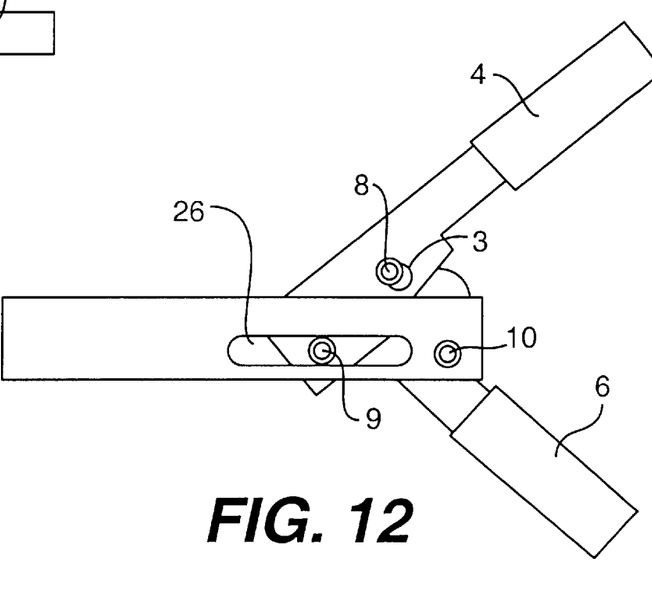
FIG. 12 is a side view of an alternative embodiment of the distal assembly of the invention.

FIG. 12 of the drawings illustrates an alternate embodiment of the invention whereby the distal end 15 of end effector 3 is further stabilized and guided during its axial displacement within clevis 2 by providing a slot 26 in the side of the clevis to accommodate a pin 9 on the proximal end of the effector 3.

The distal assembly of the invention, because of its unique engagement of the end effectors with each other and with the actuator rod within the clevis, whereby the first effector is directly attached to the actuator rod while the second end effector has a pivotal attachment between the ends of the first end effector, achieves a compact, linear collapsed configuration, compatible with an interior lumen of surgical scopes or similar devices. The extremely wide opening of the end effectors in the open configuration of up to about one hundred twenty degrees as shown, for example, in FIG. 3, greatly facilitates the taking of tissue specimens. Further, the avoidance of a direct connection between the actuator rod and the second effector while achieving opening and closing movement of both effectors permits fewer and less complex linkages and reduced size while preserving the advantages of two widely opening, actuated jaws.

The improved distal assembly of the invention has been described in connection with a bioptome having jaws for taking biopsy samples. It is to be understood that other types of end effectors, including end effectors for clamping or cutting tissue or performing any other appropriate surgical procedure, may be modified for use in accordance with the present invention. The end effector described herein is illustrative only of one preferred embodiment of the invention.

It will be apparent to those skilled in the art that various modifications and variations can be made in the assembly of the present invention without departing from the scope or spirit of the invention. Other embodiments of the invention will be apparent to those skilled in the art from consideration of the specification and examples should be considered as exemplary only, with a true scope and spirit of the invention being indicated by the following claims.

We claim:

1. A distal assembly for grasping or cutting internal body tissue, the distal assembly comprising:
    first and second end effectors pivotally engaging one another;
    a clevis having a distal end in pivotal engagement with said second end effector, said clevis having a longitudinal passage therethrough; and
    a slidable actuator disposed in said passage of said clevis, wherein a distal end of the actuator is pivotally attached to a proximal end of said first end effector in the passage of said clevis.

2. The distal assembly of claim 1 wherein said clevis has a proximal end adapted to slidably receive an elongated member engaging the proximal end of said actuator to permit axial displacement thereof to cause articulation of said first and second end effectors.

3. The distal assembly of claim 1 wherein said second end effector pivotally engages said first end effector at a point intermediate the length of the first end effector and the distal end of said clevis pivotally engages said second end effector at a point intermediate the length of the second end effector.

4. The distal assembly of claim 1 wherein said first and second end effectors have distal ends which are jaws.

5. The distal assembly of claim 1 wherein the clevis is provided with a longitudinal slot to accommodate longitudinal displacement of a pin on said first end effector.

6. The distal assembly of claim 1 wherein said first end effector is provided with a cut-out portion to accommodate the point of pivotal engagement of said second end effector with said clevis.

7. The distal assembly of claim 1 wherein axial displacement of said actuator in said passage brings said first and second effectors into linear alignment with one another such that the lateral dimensions of said effectors together are substantially the same as said clevis.

8. The distal assembly of claim 1 wherein axial displacement of said actuator in said passage brings said end effectors open to an angle greater than about 90 degrees.

9. The distal assembly of claim 6 wherein end effectors are capable of opening to about 120 degrees.

10. Surgical forceps for grasping or cutting internal tissue, comprising:
    a sheath having a distal end and a proximal end;
    an elongated member having a distal end and a proximal end, slidably disposed within said sheath;
    an end effector assembly disposed at the distal end of said sheath and comprising first and second end effectors pivotally engaging one another;
    a clevis having a proximal end engaging the distal end of the sheath and a distal end in pivotal engagement with said second end effector, said clevis having a longitudinal passage therethrough;
    a slidable actuator disposed in the passage and having a proximal end attached to the distal end of said elongated member, wherein a distal end of the actuator is pivotally attached to the proximal end of said first end effector in the passage of said clevis; and
    a manipulator attached at the proximal end of said sheath for causing axial displacement of said elongated member relative to said sheath to cause articulation of said first and second end effectors.

11. The surgical forceps of claim 10 wherein said second end effector pivotally engages said first end effector at a point intermediate the length of the first end effector and the distal end of said clevis pivotally engages said second end effector at the point intermediate the length of the second end effector.

12. The surgical forceps of claim 10 wherein said first and second end effectors have distal ends which are jaws.

13. The surgical forceps of claim 10 wherein the clevis is provided with a longitudinal slot to accommodate axial displacement of a pin on said first end effector.

14. The surgical forceps of claim 10 wherein said first end effector is provided with a cut-out portion to accommodate the point of pivotal engagement of said second end effector with said clevis.

15. The surgical forceps of claim 10 wherein axial displacement of said actuator in said passage to bring said first and second effectors into linear alignment with one another such that the lateral dimensions of said effectors together are substantially the same as that of said clevis.

16. The surgical forceps of claim 10 wherein axial displacement of said actuator is said passage brings said end effectors open to an angle greater than 90 degrees.

17. The surgical forceps of claim 14 wherein said end effectors are capable of opening to about 120 degrees.

18. An end effector assembly for use in a surgical forceps, comprising:
    first and second articulated end effectors, each having a proximal end and a distal end adapted for opposing engagement with the distal end of the other, the proximal end of the first effector being adapted for engagement with a distal end of an axially displaceable actuator and the proximal end of the second effector pivotally engaging said first effector at a point intermediate the proximal and distal ends of the first effector; the proximal end of said second end effector being adapted for pivotal engagement with the distal end of a clevis having an axial passage for accommodating said actuator.

19. The end effector assembly of claim 18 wherein articulation of said end effectors is caused by axial displacement of said actuator in the axial passage of said clevis.

20. The end effector assembly of claim 18 wherein the distal ends of said end effectors are jaws.

21. The end effector of claim 19 wherein said articulation is opening and closing together of said end effectors.

22. The end effector assembly of claim 21 wherein said end effectors are capable of opening to an angle of about 120°.

23. The end effector assembly of claim 21 wherein said end effectors close into opposed linear alignment with one another.

24. The end effector assembly of claim 18 wherein said point of pivotal engagement of the proximal end of said other end effector with said one end effector is out of axial alignment of said actuator and the proximal end of said one end effector.

* * * * *